US009992603B1

(12) United States Patent
Jain et al.

(10) Patent No.: US 9,992,603 B1
(45) Date of Patent: Jun. 5, 2018

(54) METHOD, SYSTEM AND APPARATUS FOR MEASURING HEAD SIZE USING A MAGNETIC SENSOR MOUNTED ON A PERSONAL AUDIO DELIVERY DEVICE

(71) Applicant: EmbodyVR, Inc., Redwood City, CA (US)

(72) Inventors: Kapil Jain, Santa Clara, CA (US); Abhilash Mathew, Santa Clara, CA (US)

(73) Assignee: EmbodyVR, Inc., San Mateo, CA (US)

( * ) Notice: Subject to any disclaimer, the term of this patent is extended or adjusted under 35 U.S.C. 154(b) by 0 days. days.

(21) Appl. No.: 15/811,386

(22) Filed: Nov. 13, 2017

Related U.S. Application Data

(60) Provisional application No. 62/421,285, filed on Nov. 13, 2016, provisional application No. 62/421,380, filed on Nov. 14, 2016, provisional application No. 62/424,512, filed on Nov. 20, 2016, provisional application No. 62/466,268, filed on Mar. 2, 2017, provisional application No. 62/468,933, filed on Mar. 8, 2017.

(51) Int. Cl.
*H04S 7/00* (2006.01)
*H04R 5/033* (2006.01)
*H04S 3/00* (2006.01)
*G01B 7/14* (2006.01)
*H04R 5/04* (2006.01)

(52) U.S. Cl.
CPC ............. *H04S 7/304* (2013.01); *G01B 7/14* (2013.01); *H04R 5/033* (2013.01); *H04R 5/04* (2013.01); *H04S 3/008* (2013.01); *H04S 2400/11* (2013.01)

(58) Field of Classification Search
None
See application file for complete search history.

(56) References Cited

U.S. PATENT DOCUMENTS

| 2012/0328107 A1* | 12/2012 | Nystrom | H04S 7/303 381/17 |
| 2013/0177166 A1* | 7/2013 | Agevik | H04S 1/005 381/74 |
| 2017/0332186 A1* | 11/2017 | Riggs | H04S 7/301 |

* cited by examiner

*Primary Examiner* — Paul Huber

(57) ABSTRACT

A magnetic sensor mounted on a headband of the personal audio delivery device may output a sensor signal indicative of an interaction between a magnetic field of a transducer of a personal audio delivery device and the magnetic sensor. A head size of a head on which the personal audio delivery device is worn is calculated based on the sensor signal from the magnetic sensor. Based on the head size, a non-linear transfer function is identified which characterizes how sound is transformed via the head with the calculated head size. An output signal is generated indicative of one or more audio cues to facilitate spatialization of sound associated with the output signal based on the identified non-linear transfer function. The sound associated with the output signal is output by the transducer of the personal audio delivery device.

20 Claims, 12 Drawing Sheets

METHOD, SYSTEM AND APPARATUS FOR MEASURING HEAD SIZE USING A MAGNETIC SENSOR MOUNTED ON A PERSONAL AUDIO DELIVERY DEVICE

RELATED APPLICATIONS

This disclosure claims the benefit of priority under 35 U.S.C. § 119(e) of U.S. Provisional Application No. 62/421,380 filed Nov. 14, 2016 entitled "Spatially Ambient Aware Audio Headset", U.S. Provisional Application No. 62/424,512 filed Nov. 20, 2016 entitled "Head Anatomy Measurement and HRTF Personalization", U.S. Provisional Application No. 62/468,933 filed Mar. 8, 2017 entitled "System and Method to Capture and Characterize Human Auditory Anatomy Using Mobile Device, U.S. Provisional Application No. 62/421,285 filed Nov. 13, 2016 entitled "Personalized Audio Reproduction System and Method", and U.S. Provisional Application No. 62/466,268 filed Mar. 2, 2017 entitled "Method and Protocol for Human Auditory Anatomy Characterization in Real Time", the contents each of which are herein incorporated by reference in their entireties.

This disclosure is also related to U.S. application Ser. No. 15/811,392, filed Nov. 13, 2017, entitled "Spatially Ambient Aware Personal Audio Delivery Device", U.S. application Ser. No. 15/811,295, filed Nov. 13, 2017, entitled "Image and Audio Based Characterization of a Human Auditory System for Personalized Audio Reproduction", U.S. application Ser. No. 15/811,642, filed Nov. 13, 2017, "Audio Based Characterization of a Human Auditory System for Personalized Audio Reproduction", and U.S. application Ser. No. 15/811,441, filed Nov. 13, 2017, entitled "System and Method to Capture Image of Pinna and Characterize Human Auditory Anatomy using Image of Pinna", the contents each of which are herein incorporated by reference in their entireties, the contents each of which are herein incorporated by reference in their entireties.

FIELD OF THE DISCLOSURE

The disclosure is related to consumer goods and, more particularly, to a personal audio delivery device such as a headphone arranged to facilitate determining head size of a person wearing the personal audio delivery device based on a magnetic sensor mounted on the personal audio delivery device. The head size may be used to facilitate spatial localization of sound heard by the person while wearing the personal audio delivery device.

BACKGROUND

A human auditory system includes an outer ear, middle ear, and inner ear. With the outer ear, middle ear, and inner ear, the human auditory system is able to hear sound. For example, a sound source such as a loudspeaker in a room may output sound. A pinna of the outer ear receives the sound, directs the sound to an ear canal of the outer ear, which in turn directs the sound to the middle ear. The middle ear of the human auditory system transfers the sound into fluids of an inner ear for conversion into nerve impulses. A brain then interprets the nerve impulses to hear the sound. Further, the human auditory system is able to perceive the direction where the sound is coming from. The perception of direction of the sound source is based on interactions with human anatomy. The interaction includes the sound reflecting and/or reverberating and diffracting off a head, shoulder and pinna. The interaction generates audio cues which are decoded by the brain to perceive the direction where the sound is coming from.

It is now becoming more common to listen to sounds wearing personalized audio delivery devices such as headphones, hearables, earbuds, speakers, or hearing aids. The personalized audio delivery devices outputs sound, e.g., music, into the ear canal of the outer ear. For example, a user wears an earcup seated on the pinna which outputs the sound into the ear canal. Alternatively, a bone conduction headset vibrates middle ear bones to conduct the sound to the human auditory system. The personalized audio delivery devices accurately reproduce sound. But unlike sound from a sound source, the sound from the personalized audio delivery devices does not interact with the human anatomy such that direction where the sound is coming from is accurately perceptible. The seating of the earcup on the pinna prevents the sound from the personal audio delivery device from interacting with the pinna and the bone conduction may bypass the pinna altogether. Audio cues indicative of direction is not generated and as a result the person is not able to perceive the direction where the sound is coming from.

BRIEF DESCRIPTION OF THE DRAWINGS

Features, aspects, and advantages of the presently disclosed technology may be better understood with regard to the following description, appended claims, and accompanying drawings where:

Figure 1:
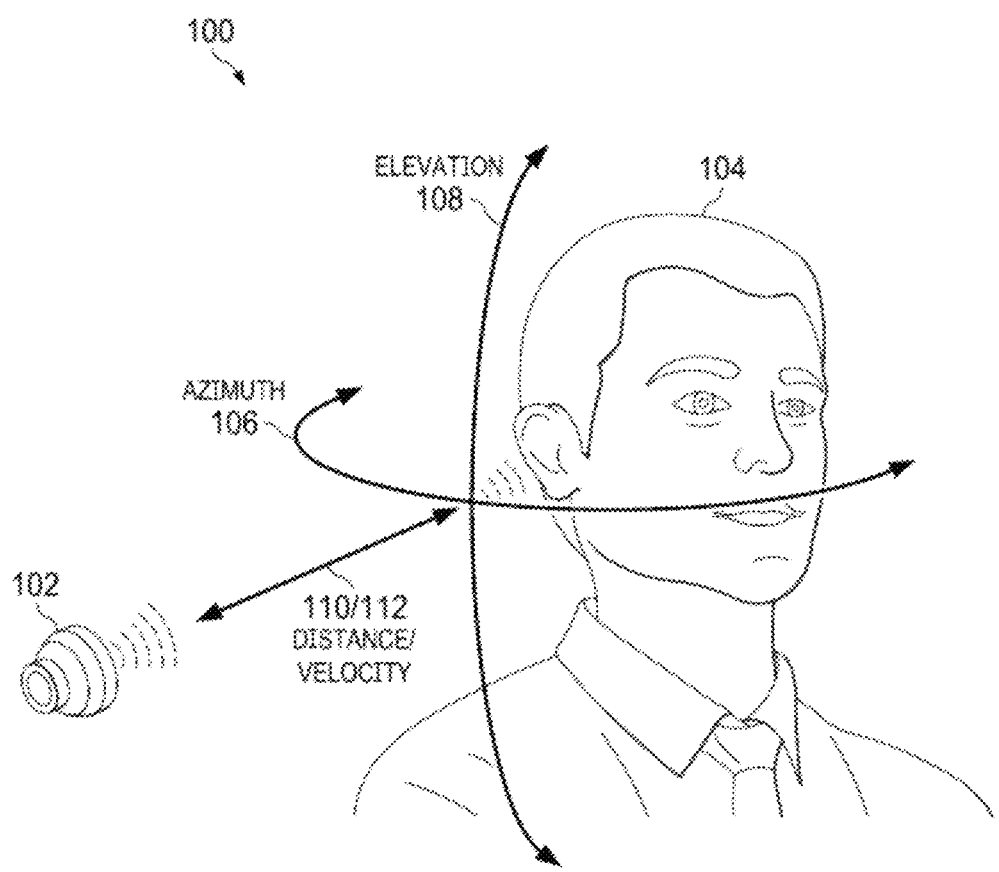
FIG. 1 is an example visualization of various parameters used for spatial localization of sound.

The drawings are for the purpose of illustrating example embodiments, but it is understood that the embodiments are not limited to the arrangements and instrumentality shown in the drawings.

DETAILED DESCRIPTION

A sound source may output sound. A direction where the sound comes from may be identified by the human auditory system using one or more audio cues. The audio cues may be sound (e.g., reflections and reverberations) indicative of a spatial location of the sound, e.g., where the sound is coming from. The audio cues may be generated from interactions between the sound, objects in an environment, and human anatomy before reaching the human auditory system. For example, reverberation and reflection from the objects may generate audio cues. Additionally, or alternatively, aspects of the human anatomy such as head shape, head size, shoulder shape, shoulder size, and outer ear (pinna) structure may generate audio cues. Each person may have different human anatomy. In this regard, the audio cues used by one person to spatially localize the sound may be different for another person.

FIG. 1 is an example visualization 100 of parameters which facilitates spatially localizing sound output by a sound source 102. One or more parameters may describe a relationship between a position of a listener 104 and the sound source 102. The parameters may include an azimuth 106, elevation 108, and a distance and/or velocity 110/112. The azimuth 106 may be an angle in a horizontal plane between the listener 104 and the sound source 102. The elevation 108 may be an angle in a vertical plane between the listener 104 and the sound source 102. The distance 110 may be a separation between the listener 104 and the sound source 102. The velocity 112 may describe a rate of movement of the sound source 104. Other parameters indicative of location may also be used.

Figure 2:
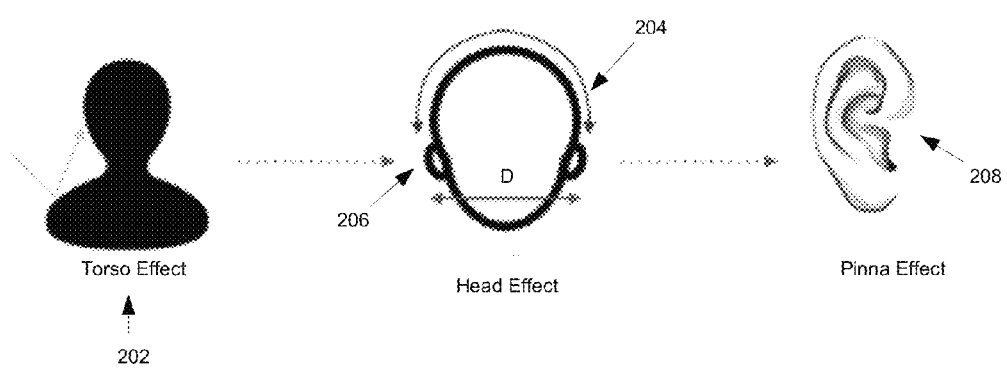
FIG. 2 shows aspects of a human anatomy in spatial localization of sound.

FIG. 2 shows aspects of a human anatomy 202-208 used in sound localization. Audio cues may be generated based on the interaction of sound with the human anatomy. The audio cues may be indicative of a spatial location from where sound comes from. The human anatomy which is illustrated includes a torso 202, head 204 with ears 206, and a pinna 208.

Reflections of sound from the torso 202 may generate an audio cue indicative of elevation and distance from where the sound is coming from, e.g., the sound source. These reflections are modeled as torso effect. Overall shape of the head 204 including ear symmetry and distance D between the ears 206 may generate an audio cue regarding azimuth and elevation from where the sound is coming from. This is modeled as head effect. Finally, how sound interacts with the shape, size, and structure of the pinna 208 may generate an audio cue regarding elevation, distance and velocity from where the sound comes from.

Figure 3:
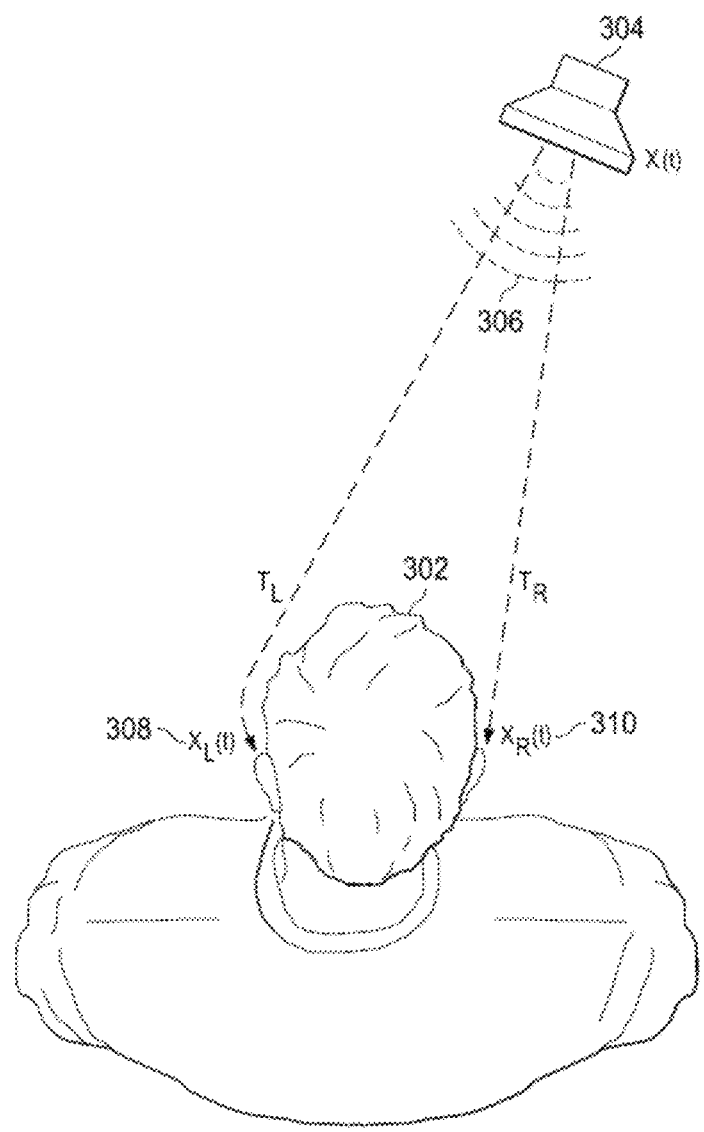
FIG. 3 shows an example of an effect of human anatomy on interaural audio cues.

FIG. 3 shows how the audio cue indicative of azimuth is generated. A person 302 may be located a certain distance away from a sound source 304. The sound source 304 may output sound 306 which is then perceived by the person at a left ear 308 and a right ear 310.

An interaural time difference (ITD) represents a difference in time arrival between the two ears 308, 310. Sound generated by sound source 304, x(t), takes $T_L$ amount of time to reach the left ear 308 and $T_R$ amount of time to reach the right ear 310. ITD represents difference between $T_L$ and $T_R$. Similarly, at any time t, sound pressure level at left ear 308 $X_L(t)$ is different from the one experienced at right ear 310 $X_R(t)$. This difference in intensity is represented by an interaural level difference (ILD) audio cue. These audio cues (ITD and ILD) may be different for a different shape and size of head. A bigger head i.e. larger distance between left and right ear 308, 310, will generate larger time and intensity difference than a smaller head.

The ITD and ILD audio cues may be directly proportional to the azimuth between the listener and the sound source. In this regard, azimuth of the sound source may be perceived. ITD and ILD, however, may be insufficient to further localize the sound source in terms of elevation, distance and velocity of the sound source.

Personal audio delivery devices such as headphones, hearables, earbuds, speakers, and hearing aids may output sound directly into the human auditory system. For example, an earcup of a headphone may be placed on the pinna and a transducer in the earcup may output sound into the ear canal. However, the earcup and headphone may cover or partially cover the pinna and head. As a result, spatial localization such as elevation, distance and velocity of the sound source may be impaired. The head and pinna might not interact with such sounds so as to generate certain audio cues to perceive the location of the sound, e.g., which direction it is coming from.

In this case, the audio cues may be artificially generated to facilitate spatial localization in terms of elevation, azimuth, distance and/or velocity. A non-linear transfer function, e.g., also referred to as a head related transfer function (HRTF) or simply transfer function, may facilitate generating the audio cues. The non-linear transfer function may characterize how sound is received by a human auditory system based on interaction with the head, torso, shoulder, pinna and other parts of the human anatomy influencing human auditory localization. The non-linear transfer function may be used to artificially generate the audio cues for determining elevation, distance and/or velocity of a sound source, among other cues.

Each person may have differences in head shape and size along with differences in features of the pinna and torso. As a result, the non-linear transfer function for one user cannot be used for another user. Such a use would result in audio cues being generated such that a sound source is perceived at a different spatial location from where it is intended to be perceived.

Embodiments described herein are directed to a personal audio delivery device arranged to determine head size. The determination of the head size by the personal audio delivery device may facilitate personalization of the non-linear transfer function for generating one or more audio cues for spatial localization of sound. The person may be able to spatialize the location of sound based on the personalized non-linear transfer function.

Figure 4:
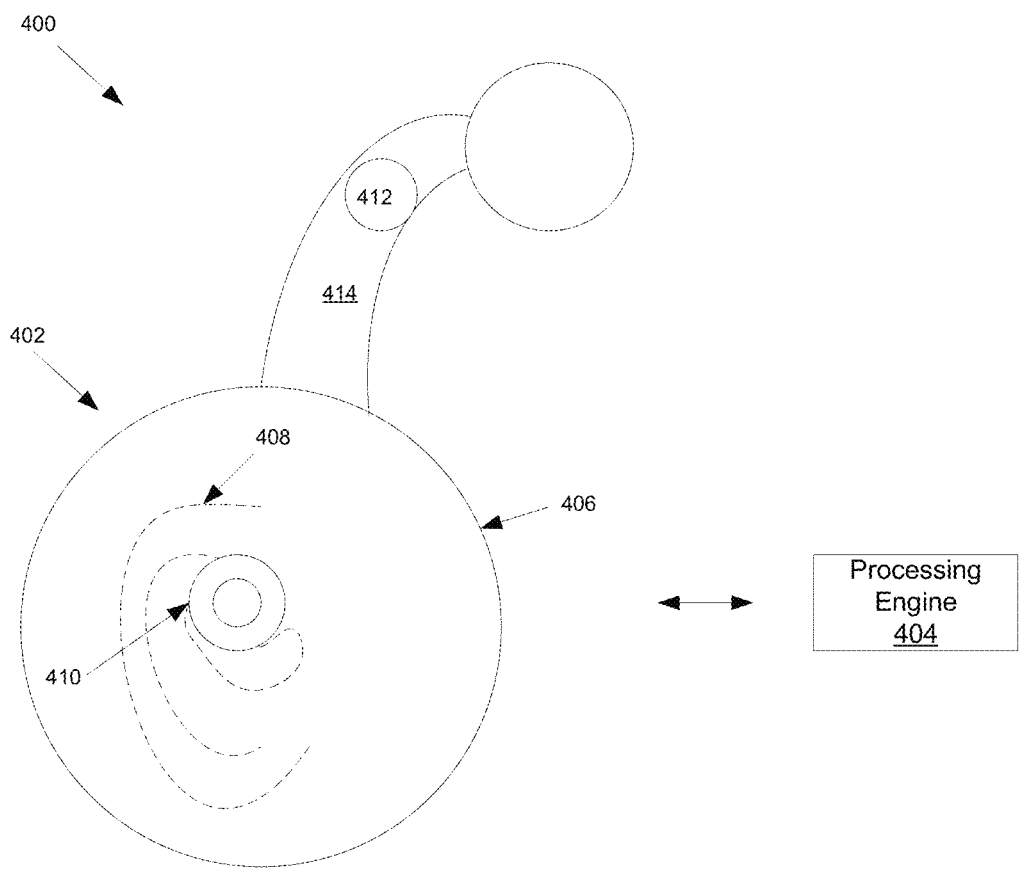
FIG. 4 shows an example system for measuring head size.

FIG. 4 illustrates an example system 400 for spatial localization. The system 400 may include the personal audio delivery device 402 and a processing engine 404.

The personal audio delivery device 402 may be a headset, hearable, or hearing aid which outputs sound such as voice and music. The personal audio delivery device 402 may have an earcup 406 which is worn on a pinna 408. The pinna 408 may not be visible externally when the earcup 404 is worn, but pinna 408 is shown as visible for purposes of illustration.

The earcup 406 may have one or more transducers 410 and one or more sensors 412. The one or more transducers 410 may be a speaker which outputs sound based on conversion of an electrical signal representative of the sound. The one or more sensors 412 may include a magnetic sensor on a headband 414 of the personal audio delivery device 402. The headband may connect two earcups. The magnetic sensor may take the form of an anisotropic magnetoresistance (AMR) sensor which changes resistance in an externally applied magnetic field or a Hall effect transducer which outputs varying voltage in response an externally applied magnetic field. The magnetic sensor may take other forms as well. The magnetic sensor may be positioned at a center of the headband 414 of the personal audio delivery device 402 such that it is equidistant from both earcups.

Figure 5A:
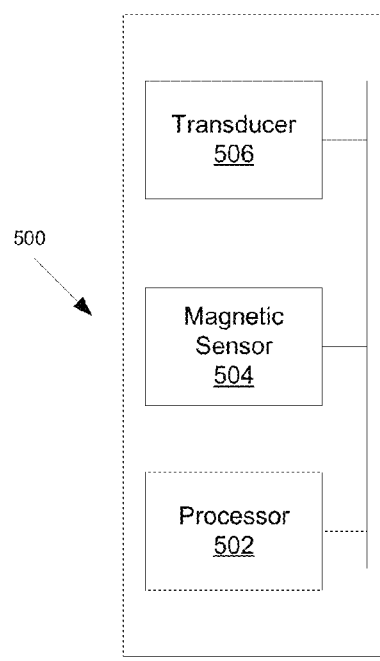
FIGS. 5A and 5B show example arrangements of a processing engine in the example system for measuring head size.
Figure 5B:
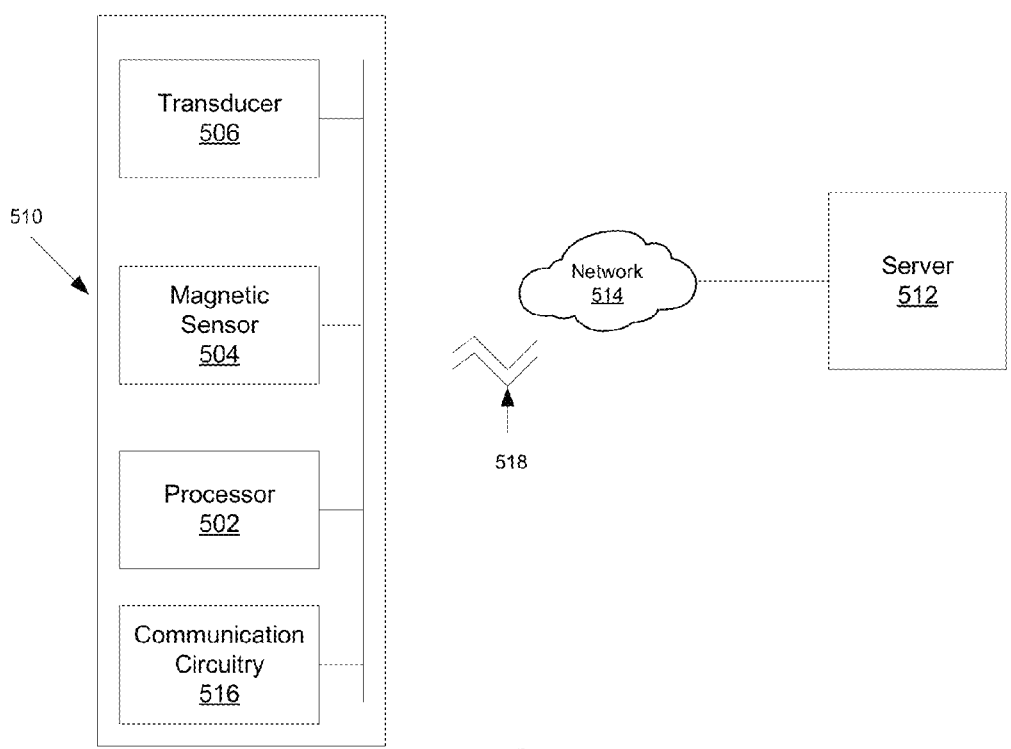

FIGS. 5A and 5B show example arrangements of the processing engine in the example system for spatial localization. The processing engine may process the signals output by the magnetic sensor. The processing engine may take the form of a processor or a server, among other arrangements.

FIG. 5A shows an arrangement of a personal audio delivery device 500 with a processing engine in the form of the processor 502. The processor 504 may be a central processing unit (CPU) local to the personal audio delivery device 500 which executes computer instructions stored in storage such as memory to process the signals associated with the one or more magnetic sensors 504 and one or more transducers 506. The processor 502 may be local when the processor 502 is integrated with the personal audio delivery device 500.

FIG. 5B shows an arrangement of a personal audio delivery device 510 and a processing engine in the form of a server 512 coupled via a network 514. The server 512 may be a network based computing system. The server 512 may process the signals associated with the one or more magnetic sensors 504 and one or more transducers 506. The server 512 may be accessible to the personal audio delivery device via the network 514. The network 514 may take the form of a wired or wireless network. The personal audio delivery device 512 may have communication circuitry 516 for communicating signals 518 with the server 512, e.g., via WiFi or Ethernet, to facilitate processing of signals associated with the transducers and/or magnetic sensors.

Latency associated with processing the signals associated with the magnetic sensor may be less with a local processor as compared the server. The latency may be less because there is no delay associated with communication to the server. The personal audio delivery device may be powered by a battery. Processing signals on the local processor may also consume power from the battery to which otherwise would be used by the personal audio delivery device to output sound when the signals associated with the magnetic sensor is processed. However, this power consumption may be minimal if the processing is performed one or a few times to determine a head size of a user of the personal audio delivery device as described in further detail below. After completing this, the head size of the user may not need to be determined again until some indication is received (e.g., a user of the personal delivery device is different). For example, a new user may provide an indication to recalculate his head size which will result in the determination of head size for the new user. Other variations are also possible.

The processing engine may take other forms as well. For example, the processing engine may take the form of the CPU local to the personal audio delivery device and the server. In other words, the processing of the signals may be performed locally by the processor at the personal audio delivery device as well as remotely at the server. Yet other variations are also possible.

Figure 6:
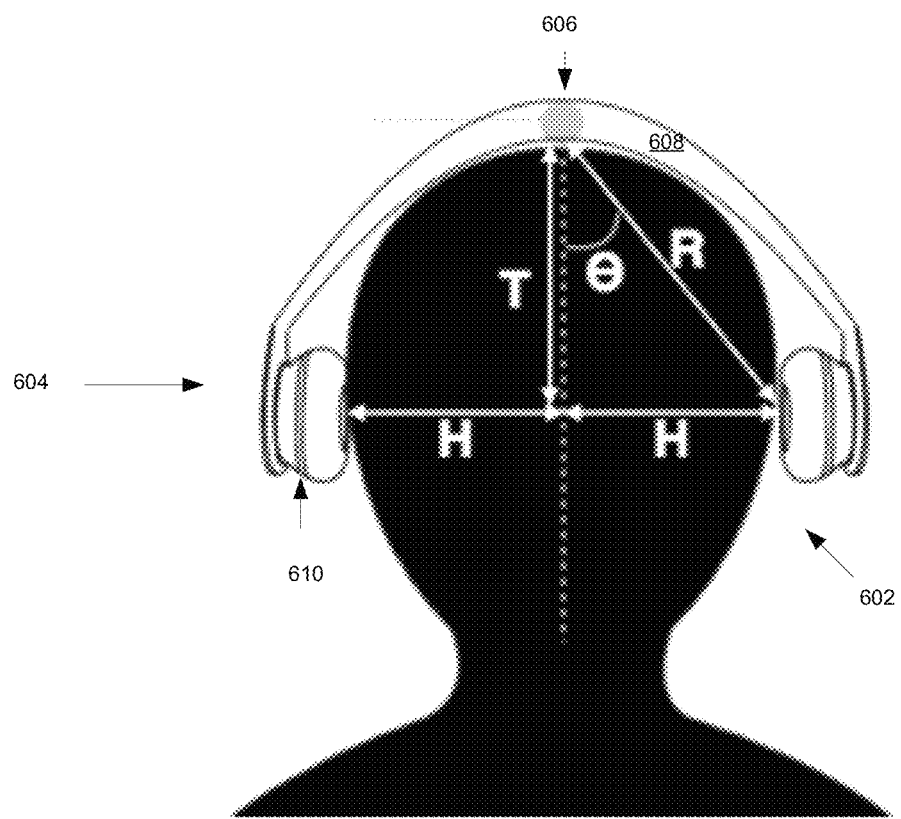
FIG. 6 shows variables associated with measuring the head size.

FIG. 6 shows a head 602 on which a personal audio delivery device 604 is worn and variables associated with determining head size. T may be known by design of the personal audio delivery device 604. Theta may be an angle between a center 606 of a headband 608 of the personal audio delivery device 604 and an earcup 610 when the personal audio delivery device is worn. T may be equivalent to a physical height of the personal audio delivery device 604 at a center of the headband 608. R may be distance between the center 606 of the headband 608 and an earcup 610. One or more of these variables may be used to determine the head size which is represented by a variable 2H, where H is distance between a center of the head 602 and the earcup 610.

Figure 7:
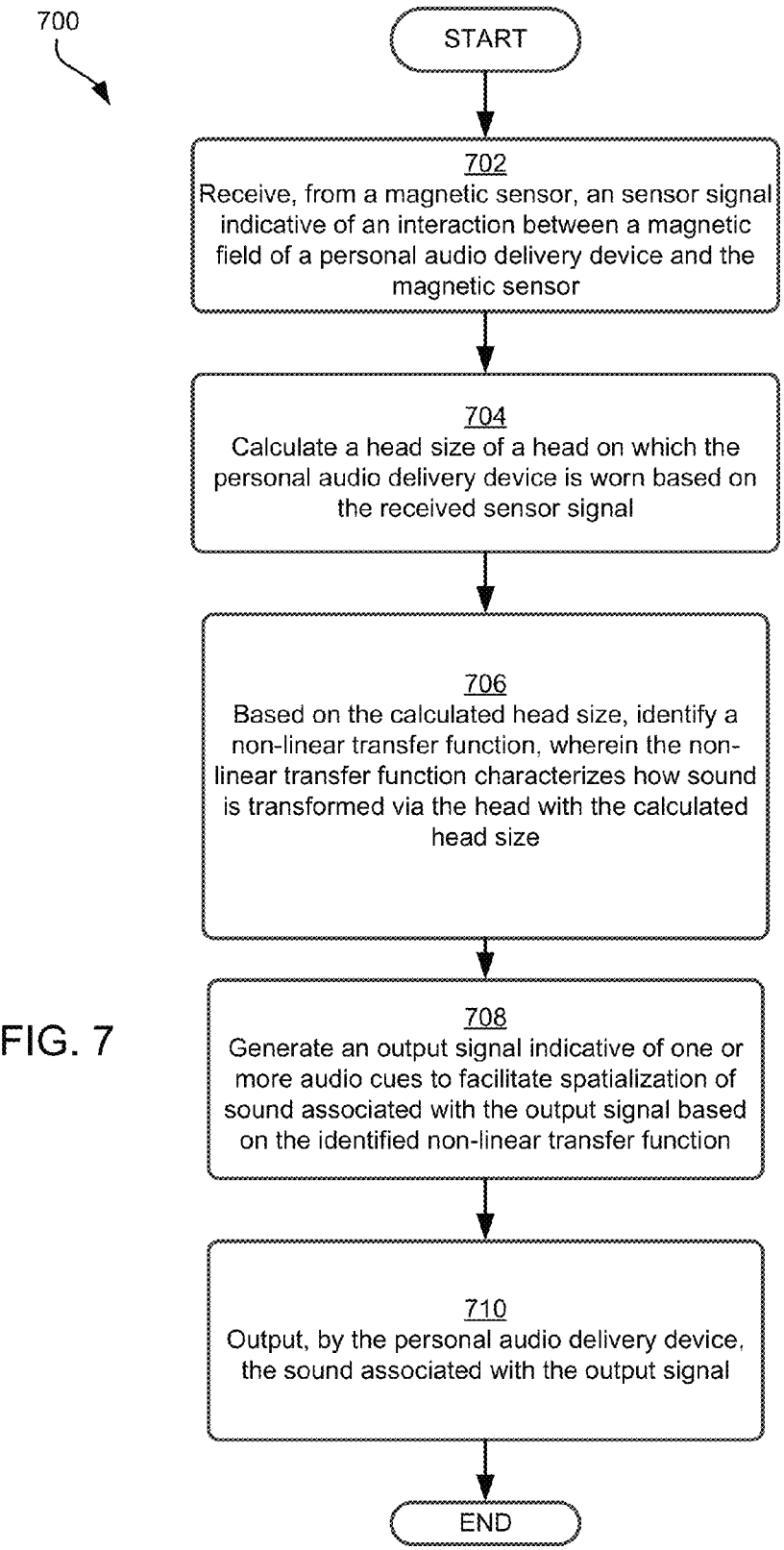
FIG. 7 is an example flow chart of functions associated with using head size to personalize audio reproduction.

FIG. 7 is an example flow chart 700 of functions associated with using head size to personalize a non-linear transfer function for a person. These functions may be performed by the example system which includes the personal audio delivery device and processing engine.

Briefly, at 702, a sensor signal may be received from a magnetic sensor indicative of an interaction between a magnetic field of a personal audio delivery device and the magnetic sensor. At 704, a head size of a head on which the personal audio delivery device is worn may be calculated based on the received sensor signal. At 706, a non-linear transfer function may be identified based on the calculated head size. The identified non-linear transfer function may characterize how sound is transformed via the head with the calculated head size. At 708, an output signal is generated indicative of one or more audio cues to facilitate spatialization of sound associated with the output signal based on the identified non-linear transfer function. At 710, the sound associated with the output signal is output by the personal audio delivery device.

An individual may wear a personal audio delivery device. The personal audio delivery device may have an earcup which the individual wears on a pinna.

Referring back, at 702, a sensor signal may be received from the magnetic sensor on the headband of the personal audio delivery device. The transducer in the earcup may have a magnet which produces the magnetic field. This magnet may be used by the transducer to output sound. This magnetic field may interact with the magnetic sensor which in turn causes the magnetic sensor to output the sensor signal indicative of the interaction. The magnetic sensor may take the form of a Hall sensor or AMR sensor, among other forms.

In the case of the Hall sensor, the sensor signal output may be associated with a distance between the Hall sensor and the earcup. The earcup may have a transducer with a magnet. The magnet produces a magnetic field. A strength of the magnetic field at the Hall sensor may be proportional to a distance to the magnet. In turn, the Hall sensor may output the sensor signal proportional to the strength of the magnetic field of the magnet. The sensor signal may have a higher voltage if the magnet field at the Hall sensor is stronger. Conversely, the sensor signal may have a lower voltage if the magnet field at the Hall sensor is weaker. In this regard, the sensor signal may be an indication of R shown in FIG. 6. The sensor signal provided by the Hall sensor indicative of R may be received by the processing engine.

In the case of the AMR sensor, the sensor signal output may be indicative of an angle by which the magnetic field passes through the AMR sensor. The sensor signal may take the form of theta shown in FIG. 6. In turn, theta may be indicative of how much the headband is stretched to fit around the head when worn. A higher theta may be indicative of the headband being stretched more to fit around the head while a lower theta may be indicative of the headband being stretched less to fit around the head.

Figure 8:
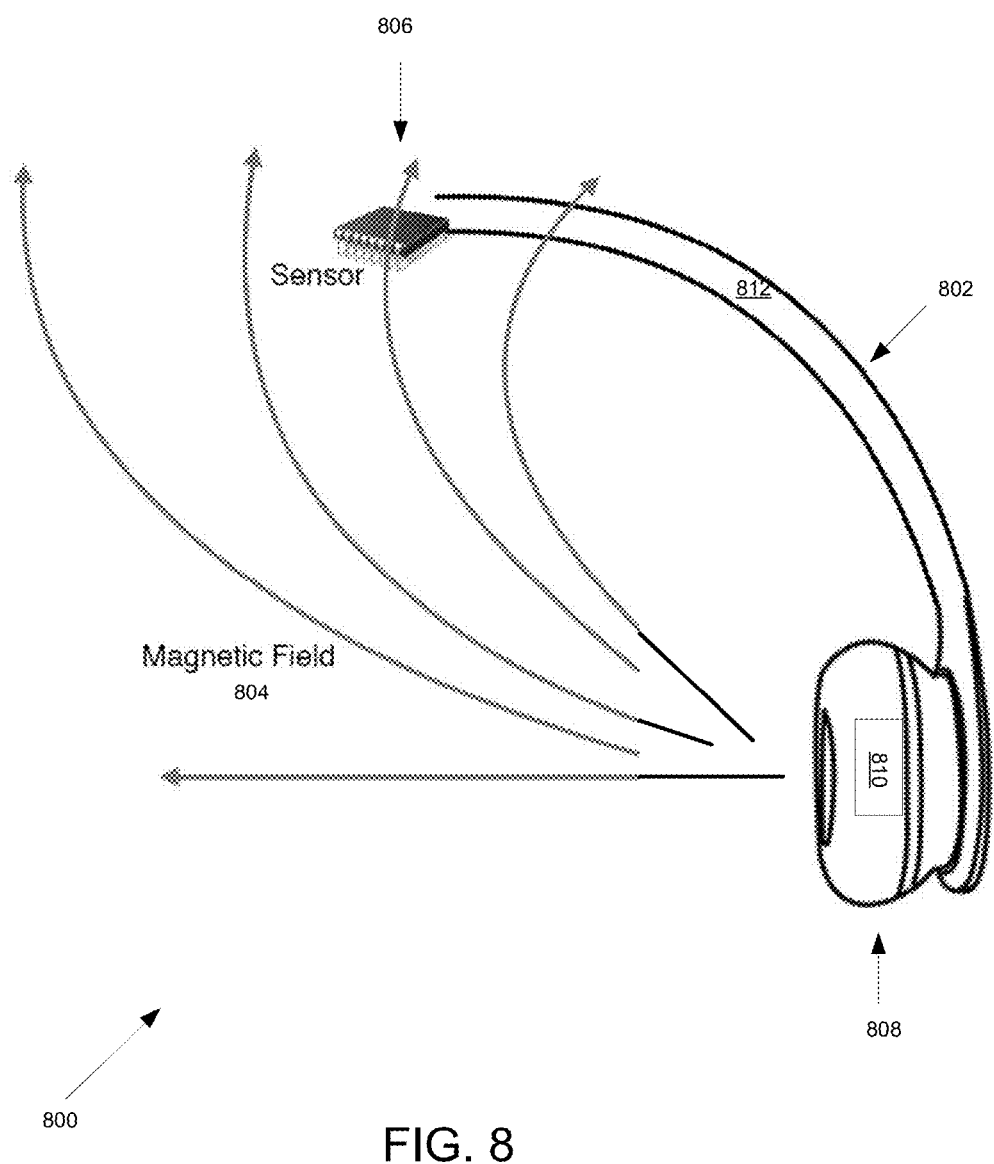
FIG. 8 shows how a magnetic field interacts with an AMR sensor.

FIG. 8 shows an arrangement 800 with a personal audio delivery device 802 and how a magnetic field 804 interacts with the AMR sensor 806. The earcup 808 may have a magnet 810. Typically, the transducer may use the magnet 810 to convert electrical signals into audible sound. A magnetic field 804 from the magnet 810 may interact with the AMR sensor 806. Lines of the magnetic field 804 associated with the magnet 810 may cross the AMR sensor 806 at different angles depending on how much a head band 812 of the personal audio delivery device 802 is stretched to fit around the head when worn. The AMR sensor 806 may output a signal indicative of an angle at which the lines of the magnetic field 808 cross the AMR sensor 806. This angle may be representative of theta. The signal provided by the AMR sensor 806 indicative of theta may be received by the processing engine.

The processing engine may receive the signal from the Hall and/or AMR sensor before any sound is output by a transducer in the earcup. This way minimal magnetic field is produced due to current flow through the transducer that would generate extraneous magnetic fields. The generation of the extraneous magnetic fields would otherwise impact measurement of the magnetic field by the magnetic sensor.

At 704, a head size of a head on which the personal audio delivery device is worn may be calculated based on the received signal.

If theta is determined at 702, the processing engine may calculate H based on the following equation:

$$H = T * \tan(\theta)$$

where H is distance from a center of the head to the earcup, T is a height of the head band of the personal audio delivery device and theta is the angle at which the magnetic field crosses the AMR sensor and which is equivalent to how far the headset is stretched around the head.

If R is determined at 702, the processing engine may calculate H based on the following equation:

$$H = \sqrt{R^2 - T^2}$$

where H is distance from a center of the head to the earcup, T is a height of the head band which is known by design of the personal audio delivery device and R is a distance between the Hall Sensor and earcup which is equivalent to how far the headset is stretched around the head.

Based on H calculated using the AMR sensor and/or Hall sensor, the head size may be calculated as:

$$\text{Head Size} = 2 * H$$

At 706, a non-linear transfer function may be identified based on the calculated head size. The non-linear transfer function may characterize how sound is transformed by the individual whose head size was calculated at 704.

Figure 9:
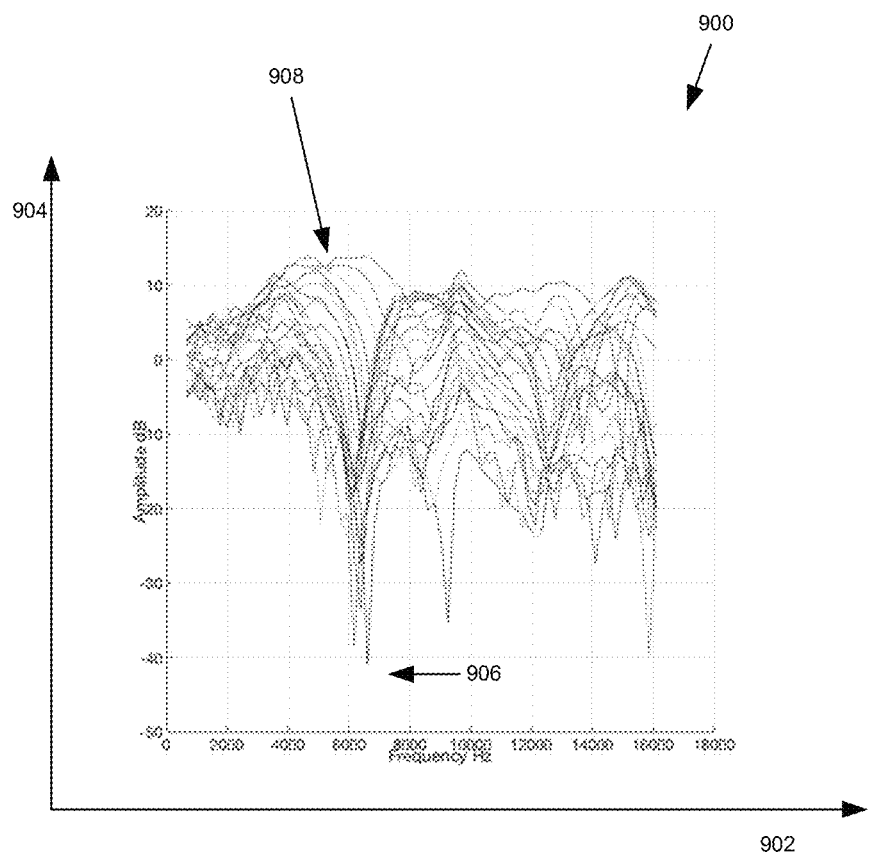
FIG. 9 shows an example of the non-linear transfer function.

FIG. 9 shows an example of the non-linear transfer function 900 for generating the missing audio cues. A horizontal axis 902 may represent a frequency, e.g., in Hz, while a vertical axis 904 may represent a frequency response, e.g., in dB. The non-linear transfer function may characterize how the head transforms sound. For example, the non-linear transfer function may define waveforms indicative of frequency responses of the head at different azimuths of the sound source and a particular elevation of the sound source. In this regard, waveforms for a given elevation and azimuth may define the frequency response of the head when sound comes from the given elevation and azimuth. Further, regions 906 may represent notches and regions 908 may represent peaks in the frequency response of the head.

The non-linear transfer functions may take other forms as well. For example, the non-linear transfer function may describe one or more of a frequency response of the head versus distance for a given azimuth and elevation and/or a frequency response of the head versus velocity for a given azimuth and elevation, among others. In other cases, the non-linear transfer function may describe a frequency response with respect to a plurality of dimensions including distance, velocity, elevation, and/or azimuth.

Figure 10A:
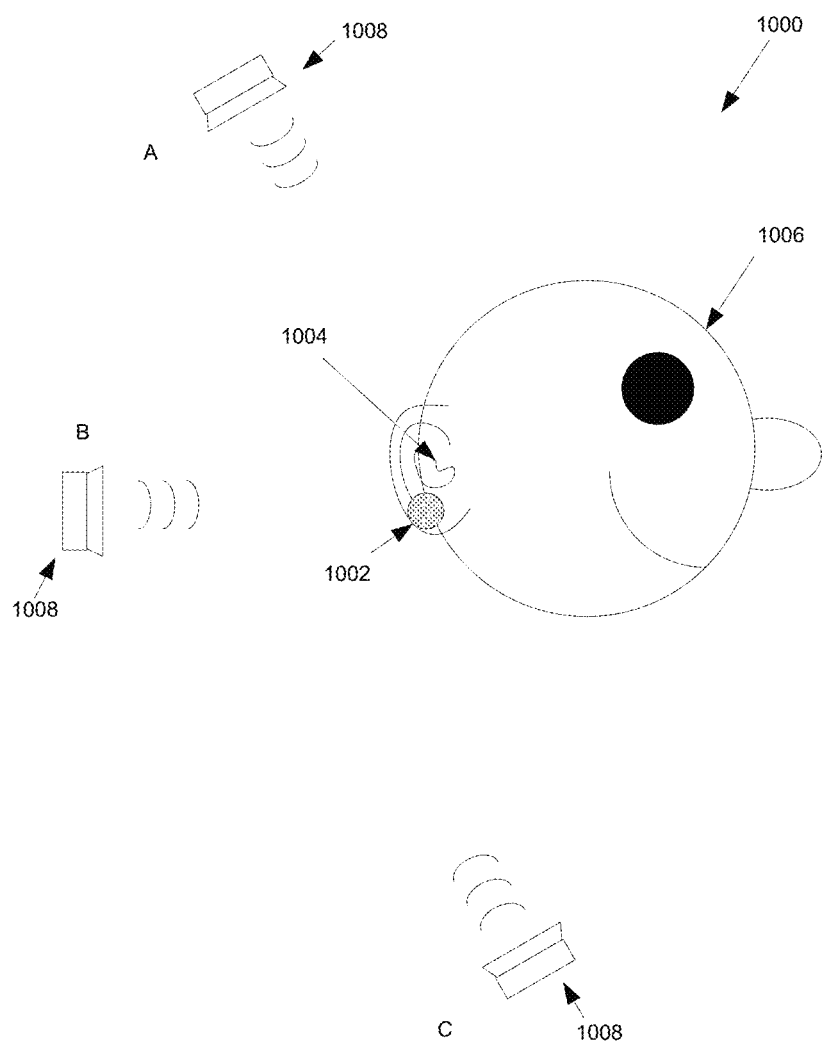
FIGS. 10A-C illustrate example arrangements associated with determining the non-linear transfer function.
Figure 10B:
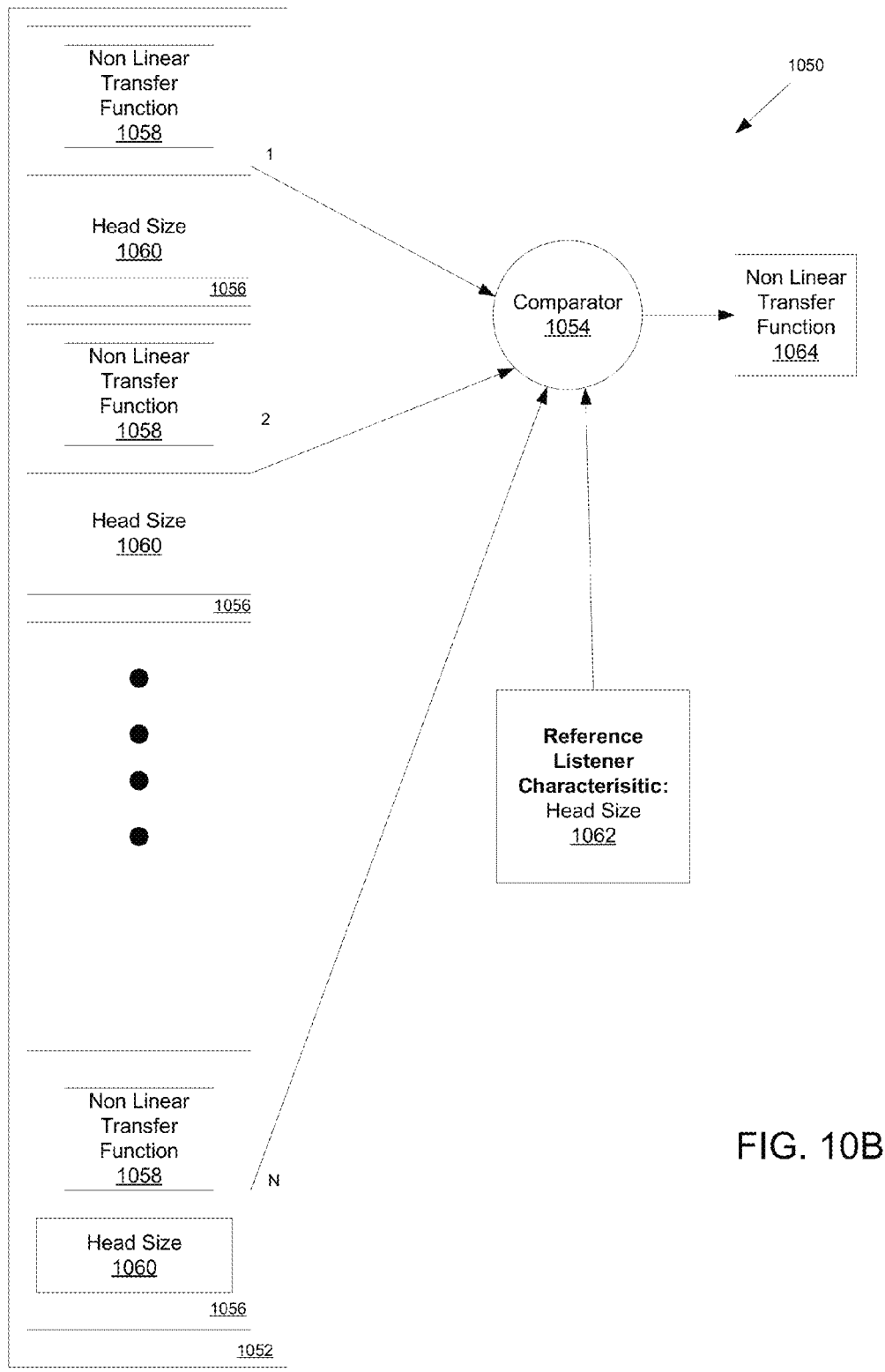
Figure 10C:
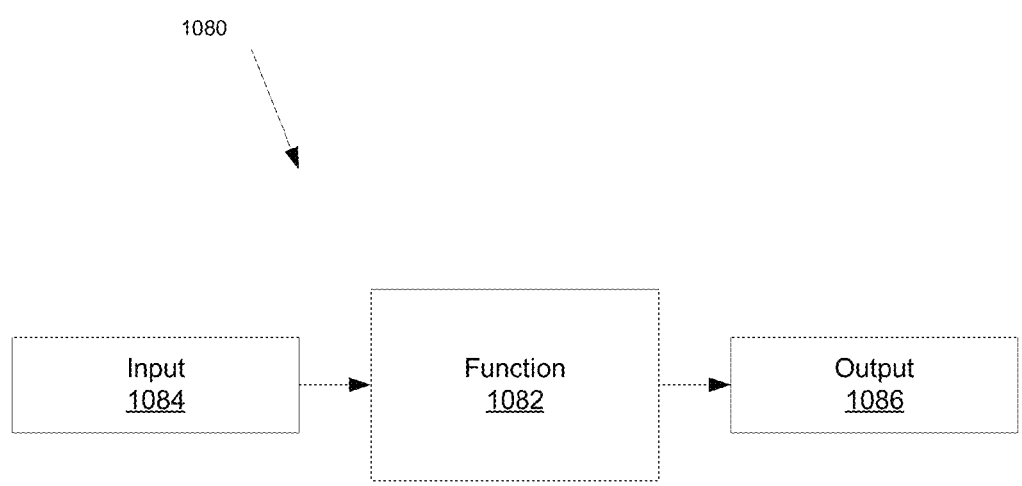

FIGS. 10A-C illustrate example arrangements associated with determining the non-linear transfer function. The non-linear transfer function may be determined in a variety of ways.

FIG. 10A illustrates an example arrangement 1000 for determining a non-linear transfer function via a direct measurement. The direct measurement may be performed during a learning process. A microphone 1002 may be placed at or near the ear canal 1004 of an individual 1006 different from whose head size was calculated at 704. Then, a sound source 1008 may be moved around the individual 1006. The sound source 1008 may be moved to a plurality of spatial locations in azimuth, elevation, distance, and/or velocity around the individual, examples which are shown as A, B, and C. A frequency response of the head 1004 measured by the microphone 1002 for the plurality of spatial locations may be indicative of the non-linear transfer function of the head. In some cases, the non-linear transfer function may be a plurality of non-linear transfer functions describing a frequency response of the head, e.g., one or more of a frequency response of the head versus azimuth for a given elevation, a frequency response of the head versus azimuth for a given distance, and/or a frequency response of the head versus azimuth for a given velocity. The non-linear transfer function may be associated with a head size of the individual under test in the learning process. The head size may be measured based on a magnetic sensor as described above or via a physical measurement such as a tape measure, among other methods.

The direct measurement process may be repeated for a plurality of individuals different from whose head size was calculated at 704 during a learning process. The direct measurements may result in determining a plurality of non-linear transfer functions where each non-linear transfer function is associated with a head size.

FIG. 10B illustrates an example arrangement 1050 for determining the non-linear transfer function for the individual whose head size was calculated at 704. The non-linear transfer function may be based on the plurality of non-linear transfer functions and associated head sizes determined during the learning process.

The example arrangement 1050 may include a database 1052 and comparator 1054. The database 1052 and comparator 1054 may reside on the personal audio delivery device, server, or some other device. The database 1052 may store the plurality of non-linear transfer functions and associated listener characteristics which correspond to the head sizes determined during the learning process. An entry 1056 in the database 1052 may define a respective non-linear transfer function 1058 and associated head size 1060 of the plurality of non-linear transfer functions and associated head sizes determined during the learning process. The database may have a plurality of entries 1:N.

The comparator 1054 may be arranged to compare each head size 1060 associated with a respective non-linear transfer function 1058 to a reference listener characteristic 1062 to identify a head size 1058 in the entries 1:N which is closest to the reference head size 1062. The reference listener characteristic 1062 may be the head size calculated at step 706. The comparator 1054 may output a non-linear transfer function 1064. The non-linear transfer function 1064 may be a non-linear transfer function 1058 associated with a head size 1060 which is closest to the head size indicated by the reference listener characteristic 1062. Mathematically, this decision may be based on the following equation (where HRTF refers to the non-linear transfer function):

Personalized $HRTF = HRTF(X_i)$, where $i$ is chosen to minimize $abs(X_i - 2*H)$ where $i = 1:N$ where N is a number of HRTFs in the plurality of HRTFs, $X_i$ is a head size associated with a respective HRTF from the plurality of HRTFs, and $2*H$ is the calculated head size.

The non-linear transfer function 1064 may be the identified non-linear transfer function at step 706. In this regard, the direct measurement may not need to be performed on the head of the individual for whom the head size is calculated at step 704 to determine the non-linear transfer function. Instead, the non-linear transfer function 1064 is based on the plurality of non-linear transfer functions and head size determined during the learning process and stored in the database 1052 and used in real time to determine the non-linear transfer function 1062.

In some examples, the non-linear transfer function for the individual whose head size was calculated at 704 may be based on a combination of one or more of the plurality of non-linear transfer functions determined during the learning process. For instance, one or more of the plurality of non-linear transfer functions may be weighed to determine non-linear transfer function for the individual whose head size was calculated at 704. The weighting may be based on a closeness of match between the calculated head size and a head size associated with a non-linear transfer function of the plurality of non-linear transfer functions. For instance, a closer match may result in a stronger weighting of the non-linear transfer function while a farther match may result in a weaker weighting of the non-linear transfer function. Then, the weighed non-linear transfer functions may be combined, e.g., summed, to form the non-linear transfer function for the individual whose head size was calculated at 704.

FIG. 10C illustrates another example arrangement 1080 for determining the non-linear transfer function for the individual whose head size was calculated at 704 without having to perform a direct measurement for the individual. The plurality of non-linear transfer functions and respective head sizes determined during the learning process may be parameterized via numerical analysis methods to define a function 1082 with an input 1084 and output 1086. Then, the head size calculated at step 704 may be provided as the input 1084 to the function 1082 and the function 1082 may provide as the output 1086 the non-linear transfer function for the individual whose head size was calculated at 704. The function may take a variety of forms.

For instance, the function 1082 may take the form of a model fit to each of the non-linear transfer functions associated with head sizes determined during the learning phase using well known data fitting techniques such as neural networks. Then, the calculated head size at 706 may be input into the model and the model may output the non-linear transfer function for the individual whose head size was calculated at 704. Mathematically, the function may be expressed as:

$$HRTF_P = f(X)$$

where x is the calculated head size and f is a function of the plurality of HRTFs.

At 708, an output signal is generated indicative of one or more audio cues to facilitate spatialization of sound associated with the output signal based on the identified non-linear transfer function. Because the sound associated with the output signal cannot properly interact with the head when the personal audio delivery device is worn, audio cues to spatially locate the sound may be missing. The non-linear transfer function may facilitate generating the audio cues to spatially locate the sound for the individual via the calculated head size at 704. For example, the identified non-linear transfer function may be modulated with a sound signal associated with the sound to form the output signal indicative of one or more audio cues. The one or more audio cues may spatialize the sound at a given spatial location. The sound signal may represent sound such as music or voice which is to be spatialized. The non-linear transfer function may be an impulse response which is convolved with the sound signal in a time domain or multiplied with the first signal in a frequency domain. The modulation of the sound signal with the non-linear transfer function may result in artificially generating these missing audio cues. In particular, audio cues for perceiving elevation, azimuth, distance and/or velocity associated with the sound may be generated.

The modulation process may be now described in more detail for spatializing sound. A direction may be associated with given sound to be spatialized. For example, metadata associated with the given sound may define a given azimuth and elevation for which the given sound is to be perceived. A frequency response of the non-linear transfer function associated with the direction may be modulated with a sound signal associated with the given sound to generate one or more audio cues that facilitate spatialization of the given sound. For example, non-linear transfer function may define one or more waveforms indicative of a frequency response of the head when sound comes from the given azimuth and elevation. The one or more waveforms may be modulated with the sound signal associated with the given sound to generate the output signal indicative of the one or more audio cues. The audio cues may enable a user to perceive the given sound coming from the given azimuth and elevation.

At 710, sound associated with the output signal may be output by the personal audio delivery device to facilitate spatial localization of the sound for the person having the head with the calculated head size. For instance, the modulated signal may be input into the transducer of the earcup. The transducer may convert the output signal to sound. The audio cues may facilitate spatialization of the sound associated with the output signal for the calculated head size.

In some examples, the transducer may output sound associated with multiple signals where sound associated with each signal is spatialized. For instance, a first signal may be modulated with a first non-linear transfer function and a second signal may be modulated with a second transfer function to generate audio cues for the first and second signal. The modulated first signal and modulated second signal may be input into the transducer. The transducer may output sound such that the sound associated with the first and second signal are each spatialized. Other variations are also possible.

The description above discloses, among other things, various example systems, methods, apparatus, and articles of manufacture including, among other components, firmware and/or software executed on hardware. It is understood that such examples are merely illustrative and should not be considered as limiting. For example, it is contemplated that any or all of the firmware, hardware, and/or software aspects or components can be embodied exclusively in hardware, exclusively in software, exclusively in firmware, or in any combination of hardware, software, and/or firmware. Accordingly, the examples provided are not the only way(s) to implement such systems, methods, apparatus, and/or articles of manufacture.

Additionally, references herein to "example" and/or "embodiment" means that a particular feature, structure, or characteristic described in connection with the example and/or embodiment can be included in at least one example and/or embodiment of an invention. The appearances of this phrase in various places in the specification are not necessarily all referring to the same example and/or embodiment, nor are separate or alternative examples and/or embodiments mutually exclusive of other examples and/or embodiments. As such, the example and/or embodiment described herein, explicitly and implicitly understood by one skilled in the art, can be combined with other examples and/or embodiments.

The specification is presented largely in terms of illustrative environments, systems, procedures, steps, logic blocks, processing, and other symbolic representations that directly or indirectly resemble the operations of data processing devices coupled to networks. These process descriptions and representations are typically used by those skilled in the art to most effectively convey the substance of their work to others skilled in the art. Numerous specific details are set forth to provide a thorough understanding of the present disclosure. However, it is understood to those skilled in the art that certain embodiments of the present disclosure can be practiced without certain, specific details. In other instances, well known methods, procedures, components, and circuitry have not been described in detail to avoid unnecessarily obscuring aspects of the embodiments. Accordingly, the scope of the present disclosure is defined by the appended claims rather than the forgoing description of embodiments.

When any of the appended claims are read to cover a purely software and/or firmware implementation, at least one of the elements in at least one example is hereby expressly defined to include a tangible, non-transitory medium such as a memory, DVD, CD, Blu-ray, and so on, storing the software and/or firmware.

EXAMPLE EMBODIMENTS

Example embodiments include:

Embodiment 1

A method comprising: receiving, from a magnetic sensor, a sensor signal indicative of an interaction between a magnetic field of a transducer of a personal audio delivery device and a magnetic sensor mounted on a headband of the personal audio delivery device; calculating a head size of a head on which the personal audio delivery device is worn based on the received sensor signal from the magnetic sensor; based on the head size, identifying a non-linear transfer function which characterizes how sound is transformed via the head with the calculated head size; generating an output signal indicative of one or more audio cues to facilitate spatialization of sound associated with the output signal based on the identified non-linear transfer function; and outputting, by the transducer of the personal audio delivery device, the sound associated with the output signal.

Embodiment 2

The method of Embodiment 2, wherein calculating the head size of the head on which the personal audio delivery device is worn based on the received sensor signal from the magnetic sensor comprises calculating the head size based on the received sensor signal indicating an angle by which a magnetic field passes through the magnetic sensor.

Embodiment 3

The method of Embodiment 1 or 2 wherein calculating the head size of the head on which the personal audio delivery device is worn based on the received sensor signal from the magnetic sensor comprises calculating the head size based on the received sensor signal indicating a strength of a magnetic field, wherein the strength is proportional to a distance between the magnetic sensor and the transducer.

Embodiment 4

The method of any of Embodiments 1-3, wherein identifying the non-linear transfer function comprises identifying the non-linear transfer function from a plurality of non-linear transfer functions associated with a respective head size closest to the calculated head size.

Embodiment 5

The method of any of Embodiments 1-4 wherein identifying the non-linear transfer function comprises inputting the calculated head size into a function which outputs the non-linear transfer function based on the calculated head size.

Embodiment 6

The method of any of Embodiments 1-5, wherein calculating the head size of the head on which the personal audio delivery device is worn is further based on a height of the personal audio delivery device.

Embodiment 7

The method of any of Embodiments 1-6, wherein the received sensor signal indicative of an interaction between the magnetic field of the transducer of the personal audio delivery device and the magnetic sensor mounted on the headband of the personal audio delivery device is based on the magnetic field of a magnet in the transducer.

Embodiment 8

The method of any of Embodiments 1-7, wherein the received sensor signal indicative of the interaction between the magnetic field of the transducer of the personal audio delivery device and the magnetic sensor is received before the sound associated with the output signal is output by the personal audio delivery device.

Embodiment 9

One or more non-transitory computer readable media comprising program code stored in memory and executable by a processor, the program code to: receive, from a magnetic sensor, a sensor signal indicative of an interaction between a magnetic field of a transducer of a personal audio delivery device and a magnetic sensor mounted on a headband of a personal audio delivery device; calculate a head size of a head on which the personal audio delivery device is worn based on the received sensor signal from the magnetic sensor; based on the head size, identify a non-linear transfer function which characterizes how sound is transformed via the head with the calculated head size; generate an output signal indicative of one or more audio cues to facilitate spatialization of sound associated with the output signal based on the identified non-linear transfer function; and output, by the transducer of the personal audio delivery device, the sound associated with the output signal.

Embodiment 10

The one or more non-transitory machine-readable media of Embodiment 9, wherein the program code to calculate the head size of the head on which the personal audio delivery device is worn based on the received sensor signal from the magnetic sensor comprises calculating the head size based on the received sensor signal indicating an angle by which a magnetic field passes through the magnetic sensor.

Embodiment 11

The one or more non-transitory machine-readable media of Embodiment 9 or 10, wherein the program code to calculate the head size of the head on which the personal audio delivery device is worn based on the received sensor signal from the magnetic sensor comprises calculating the head size based the received sensor signal indicating a strength of a magnetic field, wherein the strength is proportional to a distance between the magnetic sensor and the transducer.

Embodiment 12

The one or more non-transitory machine-readable media of any of Embodiments 9-11, wherein the program code to identify the non-linear transfer function comprises identifying the non-linear transfer function from a plurality of non-linear transfer functions associated with a respective head size closest to the calculated head size.

Embodiment 13

The one or more non-transitory machine-readable media of any of Embodiments 9-12, wherein the program code to identify the non-linear transfer function comprises inputting the calculated head size into a function which outputs the non-linear transfer function based on the calculated head size.

Embodiment 14

The one or more non-transitory machine-readable media of any of Embodiments 9-13, wherein the program code to calculate the head size of the head on which the personal audio delivery device is worn is further based on a height of the personal audio delivery device.

Embodiment 15

The one or more non-transitory machine-readable media of any of Embodiments 9-14, wherein the received sensor signal indicative of an interaction between the magnetic field of the transducer of the personal audio delivery device and the magnetic sensor mounted on the headband of the personal audio delivery device is based on the magnetic field of a magnet in the transducer.

Embodiment 16

The one or more non-transitory machine-readable media of any of Embodiments 9-15, wherein the received sensor signal indicative of the interaction between the magnetic field of the transducer of the personal audio delivery device and the magnetic sensor is received before the sound associated with the output signal is output by the personal audio delivery device.

Embodiment 17

A system comprising: a personal audio delivery device comprising a headband, a magnetic senor mounted on the headband, and a transducer; and computer instructions stored in memory and executable by a processor to perform the functions of: receiving, from the magnetic sensor, a sensor signal indicative of an interaction between a magnetic field of the transducer of the personal audio delivery device and the magnetic sensor mounted on the headband of the personal audio delivery device; calculating a head size of a head on which the personal audio delivery device is worn based on the received sensor signal from the magnetic sensor; based on the head size, identifying a non-linear transfer function which characterizes how sound is transformed via the head with the calculated head size; generating an output signal indicative of one or more audio cues to facilitate spatialization of sound associated with the output signal based on the identified non-linear transfer function; and outputting, by the transducer of the personal audio delivery device, the sound associated with the output signal.

Embodiment 18

The system of Embodiment 17, wherein the computer instructions stored in memory and executable by the processor for calculating the head size of the head on which the personal audio delivery device is worn based on the received sensor signal from the magnetic sensor comprises calculating the head size based the received sensor signal indicating an angle by which a magnetic field passes through the magnetic sensor.

Embodiment 19

The system of Embodiment 17 or 18, wherein the computer instructions stored in memory and executable by the processor for calculating the head size of the head on which the personal audio delivery device is worn based on the received sensor signal from the magnetic sensor comprises calculating the head size based the received sensor signal indicating a strength of a magnetic field, wherein the strength is proportional to a distance between the magnetic sensor and the transducer.

Embodiment 20

The system of any of Embodiments 17-19, wherein the program code to calculate the head size of the head on which the personal audio delivery device is worn is further based on a height of the personal audio delivery device.

We claim:
1. A method comprising:
receiving, from a magnetic sensor, a sensor signal indicative of an interaction between a magnetic field of a transducer of a personal audio delivery device and a magnetic sensor mounted on a headband of the personal audio delivery device;
calculating a head size of a head on which the personal audio delivery device is worn based on the received sensor signal from the magnetic sensor;
based on the head size, identifying a non-linear transfer function which characterizes how sound is transformed via the head with the calculated head size;
generating an output signal indicative of one or more audio cues to facilitate spatialization of sound associated with the output signal based on the identified non-linear transfer function; and
outputting, by the transducer of the personal audio delivery device, the sound associated with the output signal.

2. The method of claim 1, wherein calculating the head size of the head on which the personal audio delivery device is worn based on the received sensor signal from the magnetic sensor comprises calculating the head size based on the received sensor signal indicating an angle by which a magnetic field passes through the magnetic sensor.

3. The method of claim 1, wherein calculating the head size of the head on which the personal audio delivery device is worn based on the received sensor signal from the magnetic sensor comprises calculating the head size based on the received sensor signal indicating a strength of a magnetic field, wherein the strength is proportional to a distance between the magnetic sensor and the transducer.

4. The method of claim 1, wherein identifying the non-linear transfer function comprises identifying the non-linear transfer function from a plurality of non-linear transfer functions associated with a respective head size closest to the calculated head size.

5. The method of claim 1, wherein identifying the non-linear transfer function comprises inputting the calculated head size into a function which outputs the non-linear transfer function based on the calculated head size.

6. The method of claim 1, wherein calculating the head size of the head on which the personal audio delivery device is worn is further based on a height of the personal audio delivery device.

7. The method of claim 1, wherein the received sensor signal indicative of an interaction between the magnetic field of the transducer of the personal audio delivery device and the magnetic sensor mounted on the headband of the personal audio delivery device is based on the magnetic field of a magnet in the transducer.

8. The method of claim 1, wherein the received sensor signal indicative of the interaction between the magnetic field of the transducer of the personal audio delivery device and the magnetic sensor is received before the sound associated with the output signal is output by the personal audio delivery device.

9. One or more non-transitory computer readable media comprising program code stored in memory and executable by a processor, the program code to:
receive, from a magnetic sensor, a sensor signal indicative of an interaction between a magnetic field of a transducer of a personal audio delivery device and a magnetic sensor mounted on a headband of a personal audio delivery device;
calculate a head size of a head on which the personal audio delivery device is worn based on the received sensor signal from the magnetic sensor;
based on the head size, identify a non-linear transfer function which characterizes how sound is transformed via the head with the calculated head size;
generate an output signal indicative of one or more audio cues to facilitate spatialization of sound associated with the output signal based on the identified non-linear transfer function; and
output, by the transducer of the personal audio delivery device, the sound associated with the output signal.

10. The one or more non-transitory machine-readable media of claim 9, wherein the program code to calculate the head size of the head on which the personal audio delivery device is worn based on the received sensor signal from the magnetic sensor comprises calculating the head size based on the received sensor signal indicating an angle by which a magnetic field passes through the magnetic sensor.

11. The one or more non-transitory machine-readable media of claim 9, wherein the program code to calculate the head size of the head on which the personal audio delivery device is worn based on the received sensor signal from the magnetic sensor comprises calculating the head size based the received sensor signal indicating a strength of a magnetic field, wherein the strength is proportional to a distance between the magnetic sensor and the transducer.

12. The one or more non-transitory machine-readable media of claim 9, wherein the program code to identify the non-linear transfer function comprises identifying the non-linear transfer function from a plurality of non-linear transfer functions associated with a respective head size closest to the calculated head size.

13. The one or more non-transitory machine-readable media of claim 9, wherein the program code to identify the non-linear transfer function comprises inputting the calculated head size into a function which outputs the non-linear transfer function based on the calculated head size.

14. The one or more non-transitory machine-readable media of claim 9, wherein the program code to calculate the head size of the head on which the personal audio delivery device is worn is further based on a height of the personal audio delivery device.

15. The one or more non-transitory machine-readable media of claim 9, wherein the received sensor signal indicative of an interaction between the magnetic field of the transducer of the personal audio delivery device and the magnetic sensor mounted on the headband of the personal audio delivery device is based on the magnetic field of a magnet in the transducer.

16. The one or more non-transitory machine-readable media of claim 9, wherein the received sensor signal indicative of the interaction between the magnetic field of the transducer of the personal audio delivery device and the magnetic sensor is received before the sound associated with the output signal is output by the personal audio delivery device.

17. A system comprising:
a personal audio delivery device comprising a headband, a magnetic senor mounted on the headband, and a transducer; and
computer instructions stored in memory and executable by a processor to perform the functions of:
receiving, from the magnetic sensor, a sensor signal indicative of an interaction between a magnetic field of the transducer of the personal audio delivery device and the magnetic sensor mounted on the headband of the personal audio delivery device;
calculating a head size of a head on which the personal audio delivery device is worn based on the received sensor signal from the magnetic sensor;
based on the head size, identifying a non-linear transfer function which characterizes how sound is transformed via the head with the calculated head size;
generating an output signal indicative of one or more audio cues to facilitate spatialization of sound associated with the output signal based on the identified non-linear transfer function; and
outputting, by the transducer of the personal audio delivery device, the sound associated with the output signal.

18. The system of claim 17, wherein the computer instructions stored in memory and executable by the processor for calculating the head size of the head on which the personal audio delivery device is worn based on the received sensor signal from the magnetic sensor comprises calculating the head size based the received sensor signal indicating an angle by which a magnetic field passes through the magnetic sensor.

19. The system of claim 17, wherein the computer instructions stored in memory and executable by the processor for calculating the head size of the head on which the personal audio delivery device is worn based on the received sensor signal from the magnetic sensor comprises calculating the head size based the received sensor signal indicating a strength of a magnetic field, wherein the strength is proportional to a distance between the magnetic sensor and the transducer.

20. The system of claim 17, wherein the program code to calculate the head size of the head on which the personal audio delivery device is worn is further based on a height of the personal audio delivery device.

* * * * *